United States Patent
Diehnelt et al.

(10) Patent No.: US 9,757,472 B2
(45) Date of Patent: Sep. 12, 2017

(54) **PROTEAS STABILIZED ANTIBACTERIAL PEPTIDES FOR *S. AUREUS***

(71) Applicants: Chris Diehnelt, Chandler, AZ (US); Stephen Johnston, Tempe, AZ (US)

(72) Inventors: Chris Diehnelt, Chandler, AZ (US); Stephen Johnston, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 34 days.

(21) Appl. No.: 14/808,984

(22) Filed: Jul. 24, 2015

(65) Prior Publication Data
US 2016/0022832 A1 Jan. 28, 2016

Related U.S. Application Data

(60) Provisional application No. 62/029,948, filed on Jul. 28, 2014.

(51) Int. Cl.
*A61K 47/48* (2006.01)
*A61K 38/16* (2006.01)
*C07K 7/08* (2006.01)

(52) U.S. Cl.
CPC ........ *A61K 47/48246* (2013.01); *A61K 38/16* (2013.01); *C07K 7/08* (2013.01)

(58) Field of Classification Search
CPC .............................................. A61K 47/48246
See application file for complete search history.

(56) References Cited

U.S. PATENT DOCUMENTS

| | | | |
|---|---|---|---|
| 2011/0143953 A1* | 6/2011 | Johnston | C07K 16/00 506/9 |
| 2012/0021967 A1* | 1/2012 | Johnston | C07K 7/06 514/1.1 |
| 2012/0065123 A1* | 3/2012 | Johnston | G01N 33/6854 514/1.1 |
| 2014/0128280 A1* | 5/2014 | Johnston | C07K 17/06 506/9 |
| 2014/0221253 A1* | 8/2014 | Johnston | C07K 16/00 506/16 |

FOREIGN PATENT DOCUMENTS

| | | | | |
|---|---|---|---|---|
| WO | WO 2013/067160 | * | 5/2013 | ............... C07K 7/04 |
| WO | WO 2014/165240 | * | 10/2014 | ............... C07K 9/00 |

OTHER PUBLICATIONS

Domenyuk et al., 2013, A Technology for Developing Synbodies with Antibacterial Activity, PLoS One, 8(1): e54162 (11 pages).*
Lainson et al., 2015, Conjugation Approach to Produce a *Staphylococcus aureus* Synbody with Activity in Serum, Bioconjugate Chemistry, 26: 2125-2132.*
Gupta et al., 2016, Whole-Virus Screening to Develop Synbodies for the Influenza Virus, Bioconjugate Chemistry, 27: 2505-2512.*
Mahalakshmi et al., 2006, The Use of D-Amino Acids in Peptide Design, D-Amino Acids: A New Frontier in Amino Acid and Protein Research, Chapter 5.9, 415-430.*
Gupta et al., 2011, Engineering a Synthetic Ligand for Tumor Necrosis Factor-Alpha, Bioconjugate Chemistry, 22: 1473-1478.*
Stryjewski ME, Corey GR. Methicillin-Resistant *Staphylococcus aureus*: An Evolving Pathogen. Clinical Infectious Diseases. 2014;58(suppl 1):S10-S9.
Rossi F, Diaz L, Wollam A, Panesso D, Zhou Y, Rincon S, et al. Transferable Vancomycin Resistance in a Community-Associated MRSA Lineage. New England Journal of Medicine. 2014;370(16)1524-31.
Diehnelt CW. Peptide Array Based Discovery of Synthetic Antimicrobial Peptides. Frontiers in Microbiology. Dec. 2013; vol. 4, Article 402, pp. 1-3.
Brogden NK, Brogden KA. Will new generations of modified antimicrobial peptides improve their potential as pharmaceuticals? International Journal of Antimicrobial Agents. 2011;38(3)217-25.
http://www.cdc.gov/drugresistance/pdf/ar-threats-2013-508.pdf. Downloaded on Jan. 26, 2016.

* cited by examiner

*Primary Examiner* — Amber D Steele
(74) *Attorney, Agent, or Firm* — Quarles & Brady LLP; Gavin J. Milczarek-Desai

(57) ABSTRACT

Improved peptide compositions and synbody compositions are disclosed that show improved stability and antibiotic activity. The new antibacterial peptides for *S. aureus* have particular D-amino acid substitutions in order to increase protease stability while also preserving marked antibiotic activity. Thus, compositions and methods for treating infections related to *S. aureus* also are disclosed.

5 Claims, 4 Drawing Sheets

Lower case amino acids signify D-AA version of the amino acid. For example, r corresponds to D-Arg.

R = [Ac]-rWrrHkHfkrPHrkHkrGSC-[NH2]
Ac = acetyl group

Lower case amino acids signify D-AA version of the amino acid.
For example, r corresponds to D-Arg.

PROTEAS STABILIZED ANTIBACTERIAL PEPTIDES FOR S. AUREUS

CROSS-REFERENCE TO RELATED APPLICATIONS

This application claims priority to U.S. Provisional Patent Application No. 62/029,948, filed Jul. 28, 2014, the entire contents of which are incorporated herein in their entirety by reference.

STATEMENT OF GOVERNMENT RIGHTS

This invention was made with government support under W911NF-10-1-0299 awarded by the Army Research Office. The government has certain rights in the invention.

TECHNICAL FIELD

This disclosure relates to the field of antibiotics and more particularly to bivalent peptides that possess antibiotic activity.

BACKGROUND

Antimicrobial resistance of bacteria is rapidly increasing and has been declared a multinational public health crisis. One of the most critical resistant pathogens is Methicillin Resistant *Staphylococcus Aureus* (MRSA), which has developed resistance to all beta-lactam antibiotics. There are 80,000 severe MRSA infections each year in the United States that are responsible for 11,285 deaths annually (CDC Antibiotic Resistance Threats in the United States, 2013).

While new antibiotics are in development, the ones closest to market are derivatives of old antibiotics. *S. aureus* has proven remarkably resilient and developed resistance to all introduced antibiotics, including a recent report of vancomycin resistant-MRSA. This suggests that resistance will rapidly develop against these new antibiotics as well.

SUMMARY

This disclosure relates to improved bivalent peptides that are useful as antibiotics. The first generation bivalent peptide, called a synbody, was bacteriostatic while improved versions were bactericidal with low toxicity. However, these synbodies are composed of L-amino acids (L-AA) and are inherently sensitive to protease degradation, both from endogenous proteases and from those secreted from *S. aureus*.

To improve the protease stability of peptide therapeutics, selective D-amino acid (D-AA) substitution was used to produce new peptides that are resistant to degradation. However, often times the D-AA substituted antimicrobial peptides (AMP) are less active than the L-AA AMP.

Selective substitution of L-Arg and L-Lys with D-Arg and D-Lys, in conjugation with N-terminal Acylation, has been found to produce synbodies that are more protease stable and active against both MSSA and MRSA. Thus, improved peptide compositions and synbody compositions are disclosed herein that show improved stability and antibiotic activity.

Various other purposes and advantages will become clear from the description in the specification that follows. Therefore, this specification includes the features hereinafter fully described in the detailed description of the preferred embodiments, and particularly pointed out in the claims. However, such description discloses only some of the various embodiments and ways in which the invention may be practiced.

DETAILED DESCRIPTION

Figure 1:
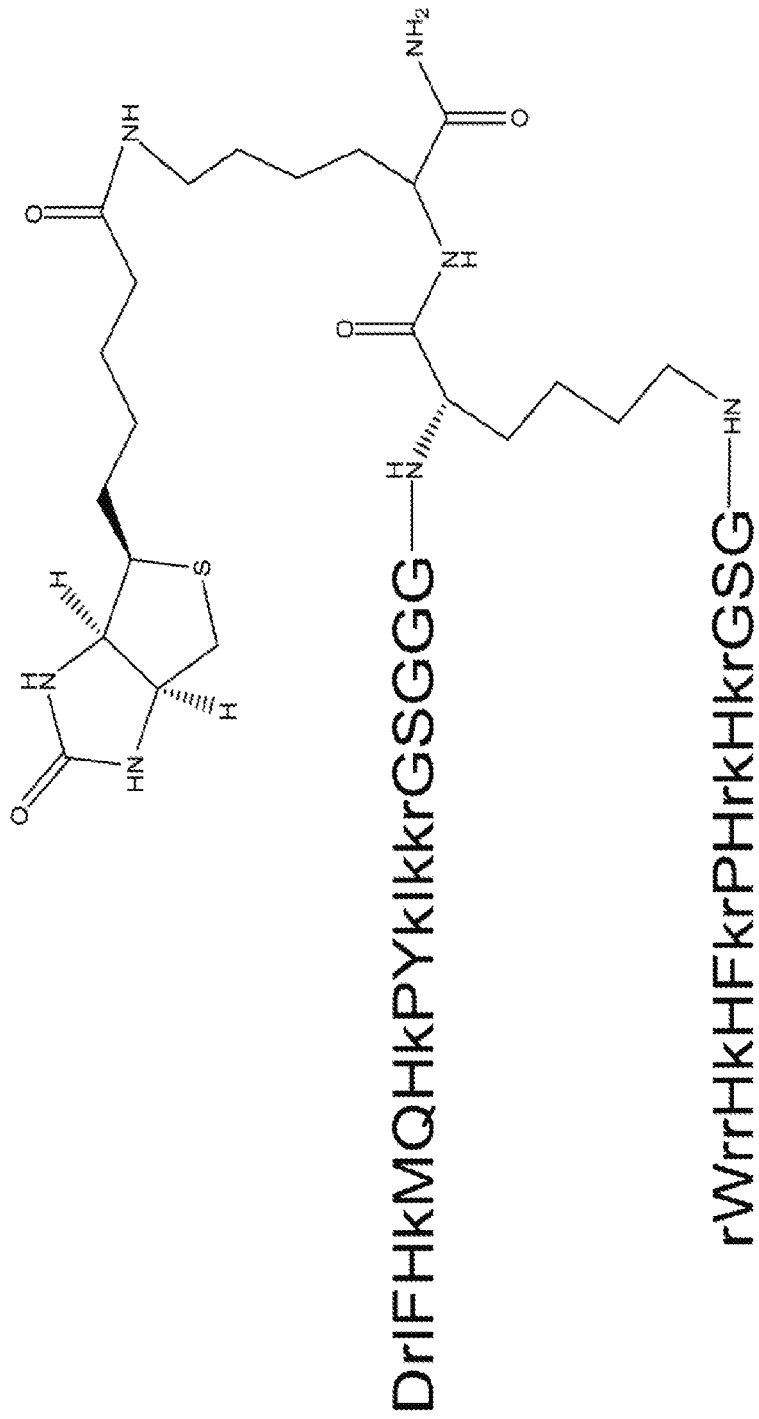
FIG. 1 depicts a D-amino acid substituted synbody, termed synbody (4).

Novel peptides and bivalent peptides (synbodies) have been produced that include selective substitution of L-Arg and L-Lys with D-Arg and D-Lys, in conjugation with N-terminal acylation. Exemplary synbodies (FIG. 1 and FIG. 3B) that are more protease stable and active against both MSSA and MRSA (Table 1 and Table 2) are further described below.

TABLE 1

Minimum inhibitory concentration (MIC), Minimum bactericidal concentration (MBC), half-life in serum, and hemolysis from synbody (4). Three different strains of MSSA and 2 different strains of MRSA were tested.

|  | MSSA (n = 3) | MRSA (n = 2) | $H_{50}$ | $t_{1/2}$ |
|---|---|---|---|---|
| Synbody (4) | 2.2 µM | 3.3 µM | >200 µM | ~130 min |

$H_{50}$ = concentration that causes 50% hemolysis
$t_{1/2}$ = in vitro half-life in mouse serum While synbody (4) is protease stable and had some bactericidal activity against MSSA, the molecule is synthesized by solid phase peptide synthesis with a low final yield. This increases the final cost of the molecule which has historically been one of the major impediments to widespread use of peptide antibiotics. To overcome this limitation, we have employed a conjugation strategy in which the purified peptide arms are conjugated to the bivalent peptide scaffold (ScO, FIG. 2) through maleimide chemistry.

Conjugation to the scaffold occurs through the thiol of a terminal Cys (either N-terminus or C-terminus) and the reaction proceeds to completion after ~12 hours incubation at room temperature. The final synbody is then purified by HPLC and the mass of the synbody is confirmed by MALDI.

Figure 3:
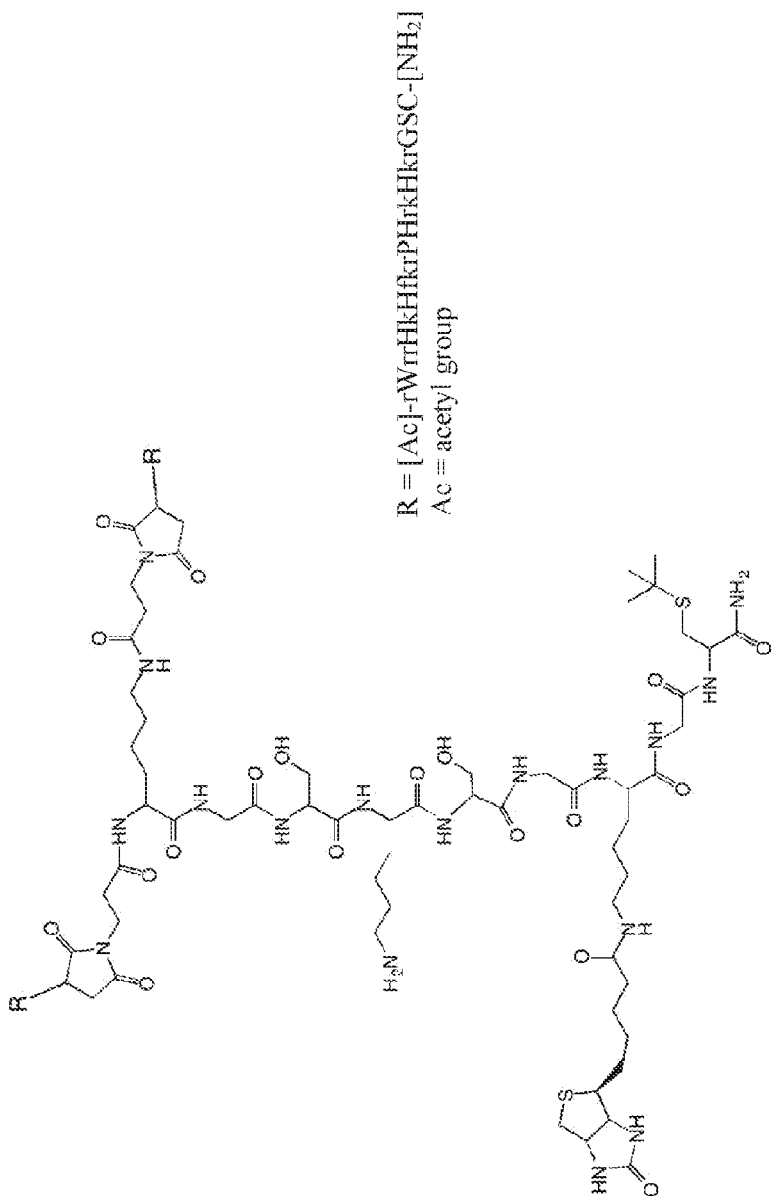
FIG. 3 depicts an amino acid sequence of peptide Ly (depicted as the R group) and a D-amino acid substituted bivalent peptide (Ly-Ly-ScO).
Figure 4:
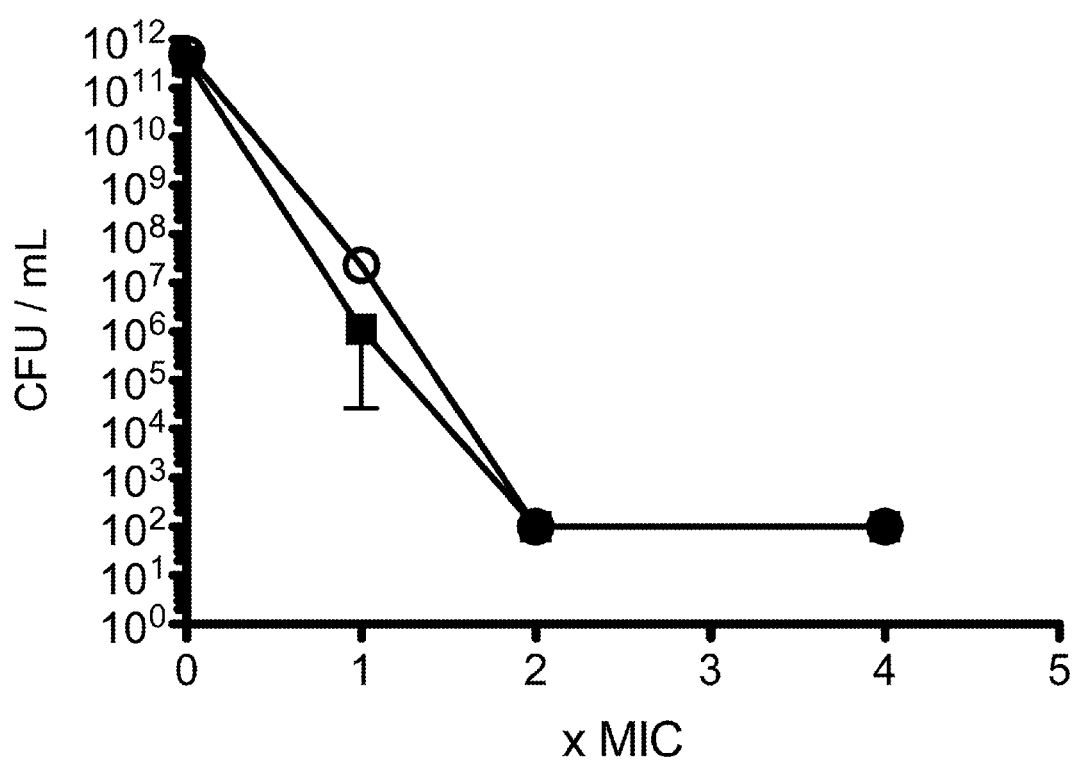
FIG. 4 shows the bactericidal activity of Ly-Ly-ScO after 14 hour incubation with either $10^7$ CFU/mL (open circles) or $10^9$ CFU/mL (black squares) MSSA culture as a function of Ly-Ly-ScO concentration.

We used this conjugation approach to conjugate the protease stabilized lytic peptide arm of synbody (4), called Ly, to ScO and produce a new anti-*S. aureus* peptide (Ly-Ly-ScO, FIG. 3). Lower case amino acids signify D-AA version of the amino acid. For example, r corresponds to D-Arg. To produce Ly-Ly-ScO, 2.2 molar equivalents of peptide (FIG. 3) were added to 1 equivalent of ScO in aqueous buffer (1×phosphate buffered saline) at pH 7. The reaction incubated at room temperature for 24 hours and was then purified using reverse phase HPLC with standard methods.

TABLE 2

MIC, MBC, half-life in serum, and hemolysis from Ly-Ly-Sc0.

| | MIC (µM) | | MBC (µM) | | |
| | MSSA | MRSA (USA300) | MSSA | $t_{1/2}$ | $H_{50}$ |
|---|---|---|---|---|---|
| Ly-Ly-Sc0 | 12.5 | 6.25 | 12.5 | not tested | >500 uM |

Figure 2:
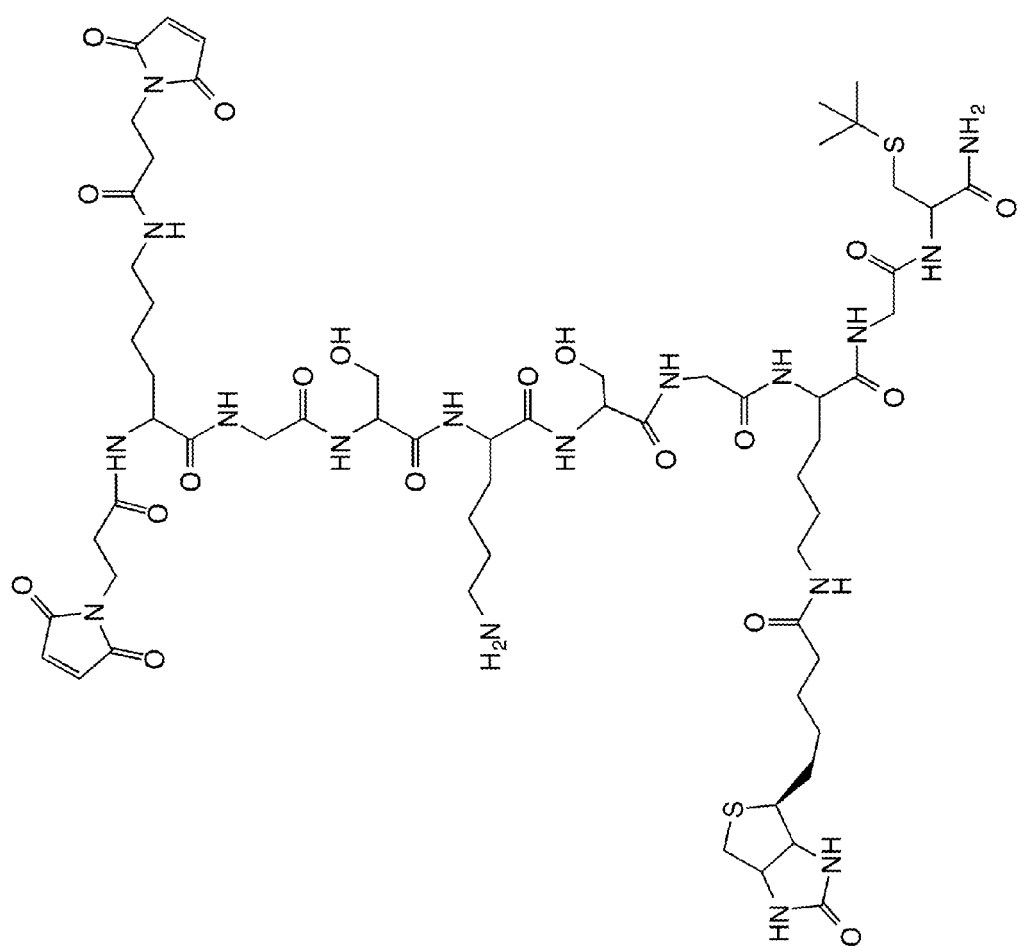
FIG. 2 depicts a bivalent scaffold for synbody construction (ScO).

Additionally, we have developed new peptides of mixed D/L AA composition that are conjugated using the ScO bivalent peptide scaffold (FIG. 2). These peptides have similar activities against MSSA and are also bactericidal, with low red blood cell toxicity. Thus, methods of treating *S. aureus* infections involve administering (by any known way) an effective amount of peptide or synbody described herein to an infected patient or subject.

TABLE 3

MIC, Minimum bactericidal concentration (MBC), and hemolysis of D/L-AA composition peptides.

| | | MIC (µM) (MSSA) | MBC (µM) (MSSA) | $H_{50}$ (µM) |
|---|---|---|---|---|
| D1-D1-ScO | CSGkkRRHHrrkkRrHHrrK-ScO-CSGkkRRHHrrkkRrHHrrK | 10 | 5 | >500 |
| D2-D2-ScO | CSGRrkrPrrkrPRrkRPRr-ScO-CSGRrkrPrrkrPRrkRPRr | 5 | 5 | >500 |
| D2-88-ScO | CSGRrkrPrrkrPRrkRPRr-ScO-CSGEMWAIMPPIIKPDNKGH | 50 | 50 | >500 |
| D1 | CSGkkRRHHrrkkRrHHrrK | <50 | | n.t. |
| D2 | CSGRrkrPrrkrPRrkRPRr | <50 | | n.t. |
| 88 | CSGEMWAIMPPIIKPDNKGH (SEQ ID NO. 1) | n.t. | | n.t. | n.t. = not tested.
Lower case amino acids signify D-AA version of the amino acid. For example, r corresponds to D-Arg.

It further is contemplated that the novel and inventive compositions described herein will be used in treatment methods not practiced on the human body. For example, animals may be treated.

Various changes in the details and components that have been described may be made by those skilled in the art within the principles and scope of the invention herein described in the specification and defined in the appended claims. Therefore, while the content above has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent processes, compositions, and products.

What is claimed is:

1. A bactericidal composition comprising a peptide scaffold ScO:

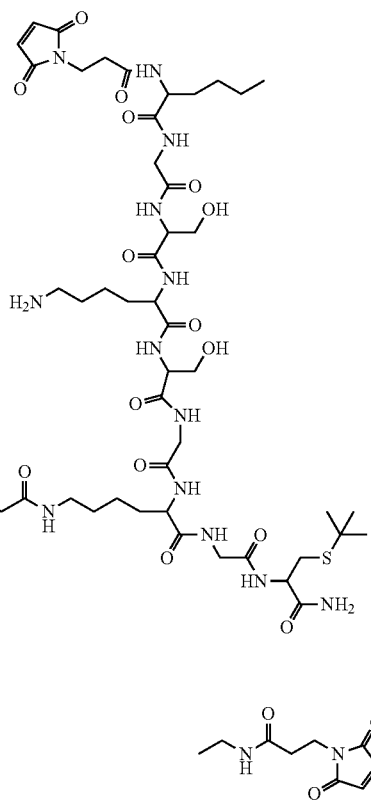

conjugated to at least one other peptide having at least one D-amino acid.

2. The composition of claim 1, wherein said composition comprises synbody Ly-Ly-ScO:

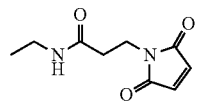

SEQUENCE LISTING

<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: potential control peptide

<400> SEQUENCE: 1

Cys Ser Gly Glu Met Trp Ala Ile Met Pro Pro Ile Ile Lys Pro Asp
1               5                   10                  15

Asn Lys Gly His
            20

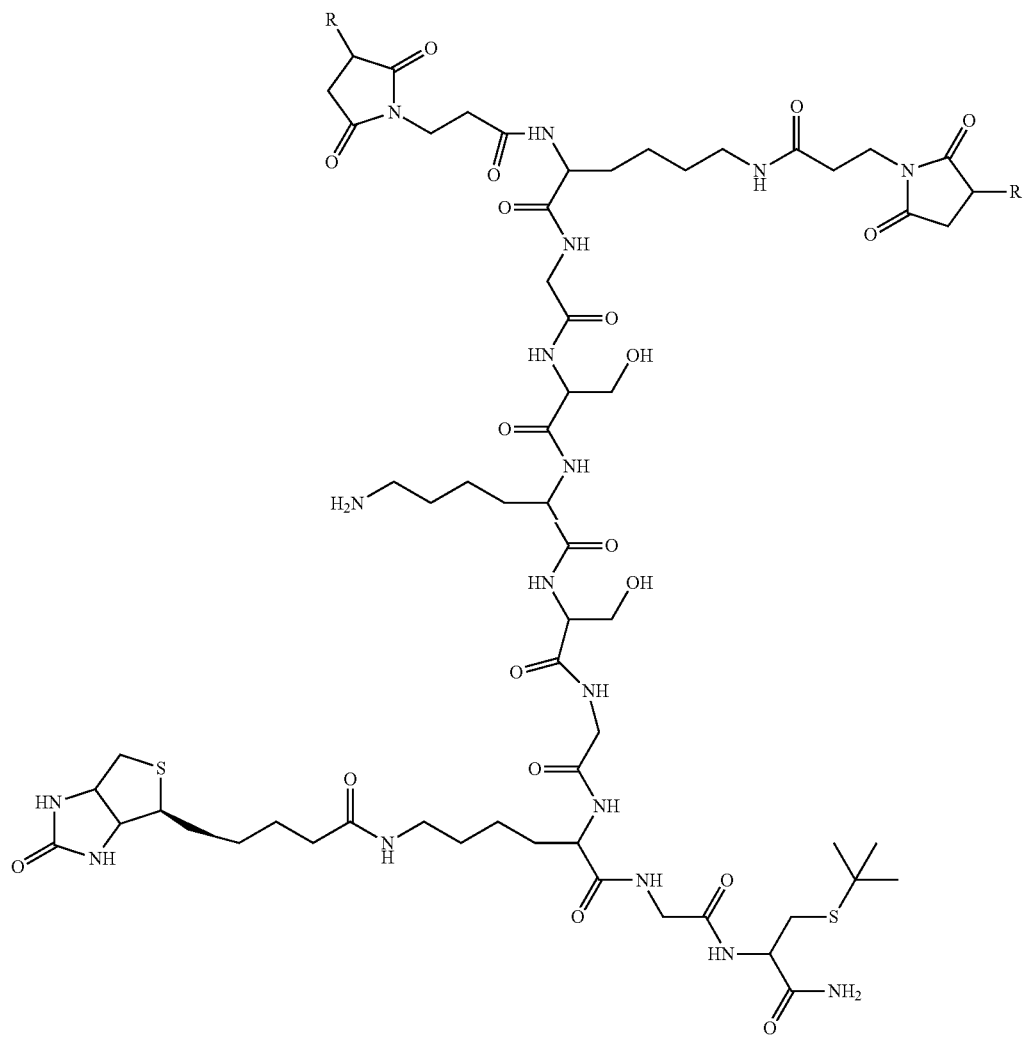

R = [Ac]-rWrrHkHfkrPHrkHkrGSC-[NH$_2$]
Ac = acetyl group wherein lowercase letters represent D amino acids.

3. The composition of claim 1, wherein said composition is selected from the group consisting of synbody D1-D1-ScO (CSGkkRRHHrrkkRrHHrrK-ScO-CSGkkRRHHrrk-kRrHHrrK), synbody D2-D2-ScO (CSGRrkrPrrkrPRrkRPRr-ScO-CSGRrkrPrrkrPRrkRPRr), and synbody D2-88-ScO (CSGRrkrPrrkrPRrkRPRr-ScO-CSGEMWAIMPPIIKPDNKGH), wherein lowercase letters represent D amino acids.

4. A method of treating an *S. aureus* infection, comprising the step of administering an effective amount of synbody Ly-Ly-ScO:

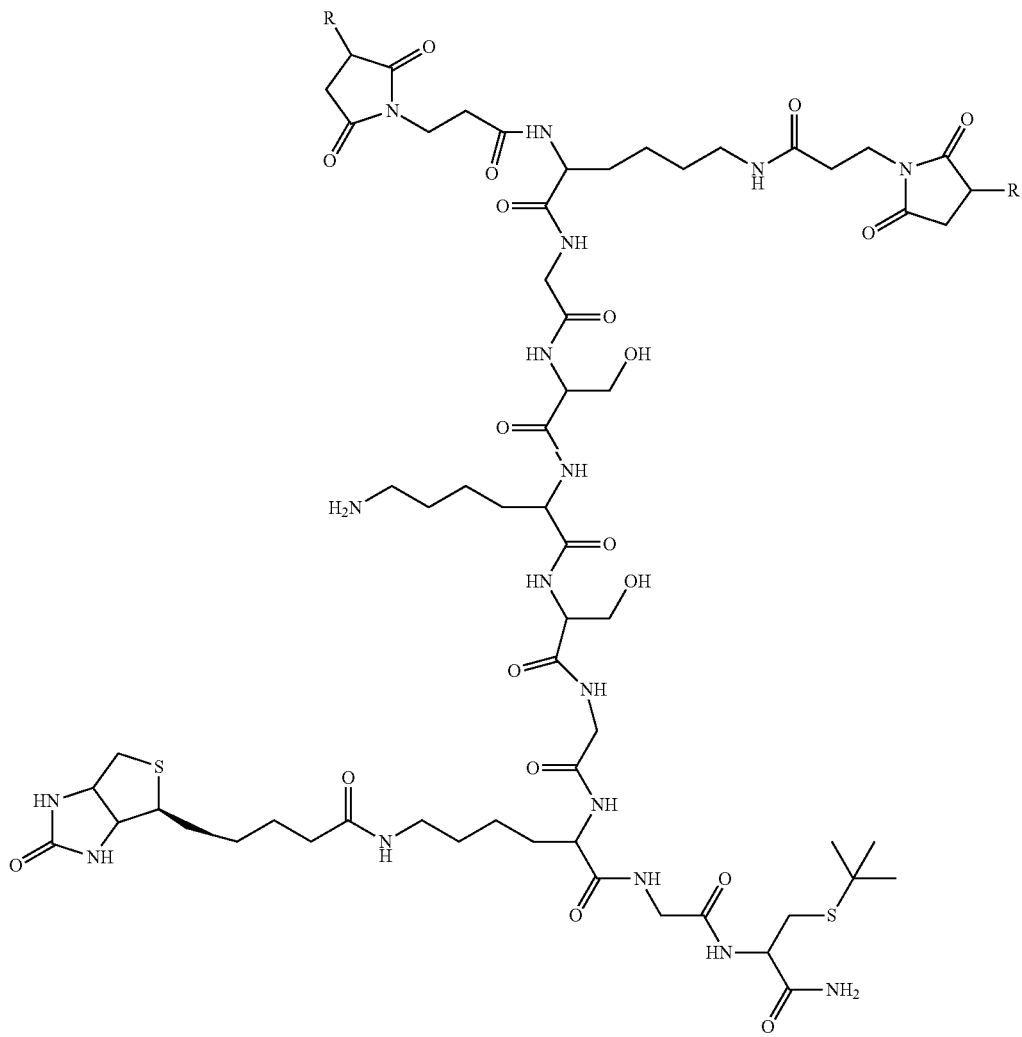

R = [Ac]-rWrrHkHfkrPHrkHkrGSC-[NH₂]
Ac = acetyl group to an infected subject, wherein lowercase letters represent D amino acids.

5. A method of treating an *S. aureus* infection, comprising the step of administering an effective amount of synbody D1-D1-ScO, (CSGkkRRHHrrkkRrHHrrK -ScO-CSGkkRRHHrrkkRrHHrrK), synbody D2-D2-ScO (CSGRrkrPrrkrPRrkRPRr-ScO-CSGRrkrPrrkrPRrkRPRr), and synbody D2-88-ScO (CSGRrkrPrrkrPRrkRPRr -ScO-CSGEMWAIMPPIIKPDNKGH), wherein lowercase letters represent D amino acids, to an infected subject, and wherein ScO comprises:

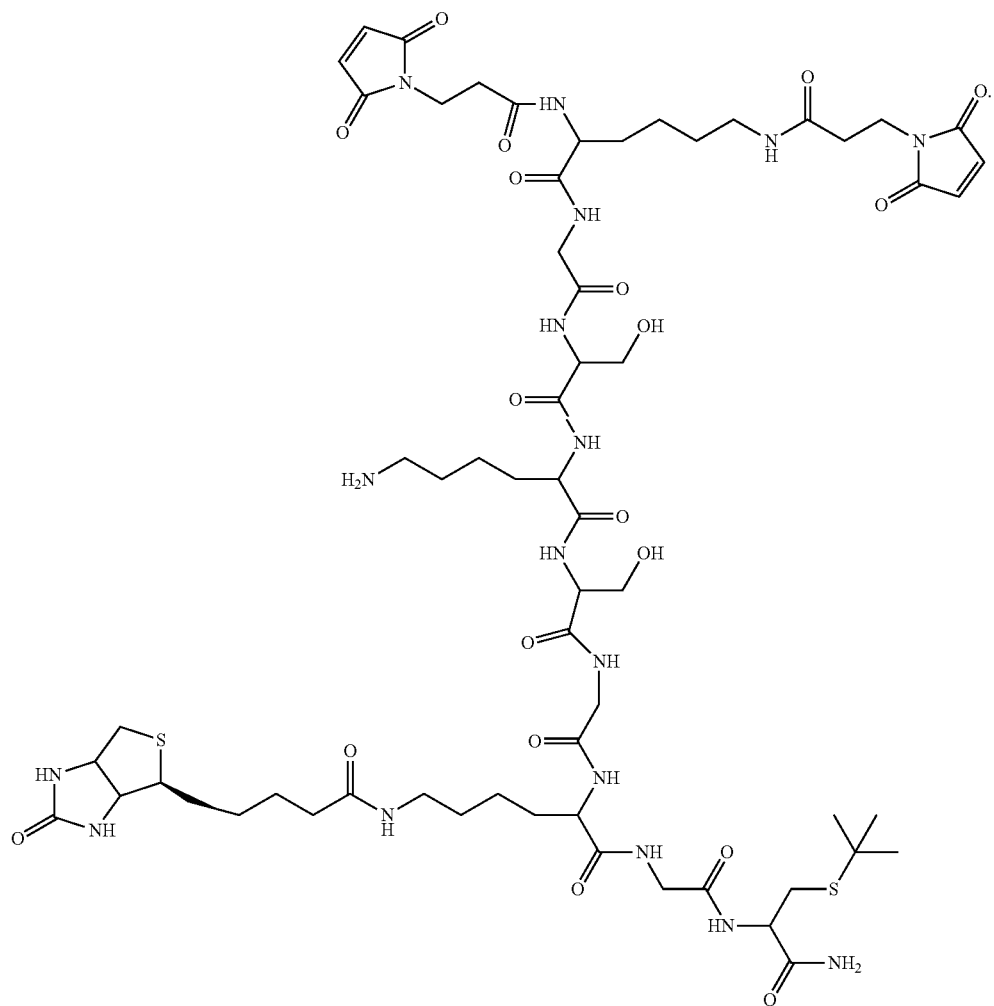 [SMILES: CC(C)(C)SCC(NC(=O)CNC(=O)C(CCCCNC(=O)CCCC[C@@H]1SCC2NC(=O)NC21)NC(=O)CNC(=O)C(CO)NC(=O)C(CCCCN)NC(=O)C(CO)NC(=O)CNC(=O)C(CCCCNC(=O)CCN1C(=O)C=CC1=O)NC(=O)CCN1C(=O)C=CC1=O)C(N)=O]
* * * * *